US007625879B2

(12) United States Patent
Belmant et al.

(10) Patent No.: US 7,625,879 B2
(45) Date of Patent: *Dec. 1, 2009

(54) PHOSPHOHALOHYDRINS, PROCESS FOR THE PRODUCTION THEREOF AND USE THEREOF

(75) Inventors: Christian Belmant, Six-Fours-les-Plages (FR); Jean-Jacques Fournie, Corronsac (FR); Marc Bonneville, Vertou (FR); Marie-Alix Peyrat, Saint-Sebastien sur Loire (FR)

(73) Assignee: Institut National de la Sante et de la Recherche Medicale, Paris (FR)

( * ) Notice: Subject to any disclaimer, the term of this patent is extended or adjusted under 35 U.S.C. 154(b) by 174 days.

This patent is subject to a terminal disclaimer.

(21) Appl. No.: 11/512,688

(22) Filed: Aug. 30, 2006

(65) Prior Publication Data

US 2006/0287281 A1      Dec. 21, 2006

Related U.S. Application Data

(60) Continuation of application No. 10/682,990, filed on Oct. 14, 2003, now Pat. No. 7,109,183, which is a division of application No. 09/786,054, filed as application No. PCT/FR99/02058 on Aug. 27, 1999, now Pat. No. 6,660,723.

(30) Foreign Application Priority Data

Sep. 1, 1998     (FR)     .................................. 98 10913

(51) Int. Cl.
| | |
|---|---|
| *A61K 31/66* | (2006.01) |
| *A01N 57/00* | (2006.01) |
| *G01N 33/00* | (2006.01) |
| *C12N 5/06* | (2006.01) |
| *C12N 5/16* | (2006.01) |
| *A01N 65/00* | (2006.01) |
| *C07D 301/36* | (2006.01) |
| *C07D 303/02* | (2006.01) |
| *C07C 321/00* | (2006.01) |
| *C07C 323/00* | (2006.01) |
| *C07C 381/00* | (2006.01) |

(52) U.S. Cl. ...................... 514/75; 514/129; 435/7.24; 435/332; 424/93.71; 549/202; 558/152

(58) Field of Classification Search ........................ None
See application file for complete search history.

(56) References Cited

U.S. PATENT DOCUMENTS

| | | | |
|---|---|---|---|
| 5,639,653 A | 6/1997 | Bloom et al. | |
| 6,660,723 B1 | 12/2003 | Belmant et al. | |
| 7,109,183 B2 * | 9/2006 | Belmant et al. | ............... 514/75 |

FOREIGN PATENT DOCUMENTS

WO     WO 95/20673     8/1995

WO     WO2006/067635 A2 *     6/2006

OTHER PUBLICATIONS (R) Kabelitz et al., "Perspectives of [gamma delta] T Cells in Tumor Immunology," *Cancer Research*, 67(1), 5-8 (Jan. 1, 2007).*
Tanaka, Y. et al. "Natural and Synthetic Non-Peptide Antigens Recognized by Human γδ T Cells"*Nature*, May 11, 1995, pp. 155-158, vol. 375.
Wesch, D. et al. "Comparative Analysis αβ and γδ T Cell Activation by *Mycobacterium Tuberculosis* and Isopentenyl Pyrophosphate" *Euro. J. Immunol.*, 1997, pp. 952-956, vol. 27, No. 4.
Burk, M.R. et al., "Human Vγ-Vδ2 Cells are Stimulated in a Cross-Reactive Fashion by a Variety of Phosphorylated Metabolites" *Euro. J. Immunol.*, 1995, pp. 2052-2058, vol. 25, No. 7.
Schoel, B. et al. "Phosphate is Essential for Stimulation of Vγ9Vδ2 T Lymphocytes by Mycobacterial Low Molecular Weight Ligand" *Euro. J. Immunol.*, 1994, pp. 1886-1892, vol. 24, No. 8.
Dhe-Paganon, S. et al. "Mechanism of Mevalonate Pyrophosphate Decarboxylase: Evidence for a Carbocationic Transition State" *Biochemistry*, Nov. 15, 1994, pp. 13355-13362, vol. 33, No. 4.
Poccia, F. et al. "γδ T Cell Activation or Anergy During Infections: The Role of Non-Peptidic TCR Ligands and HLA Class I Molecules" *Journal of Leukocyte Biology*, Sep. 1997, pp. 1-5, vol. 62.
Constant, P. et al. "The Antituberculous *Mycobacterium Bovis* BCG Vaccine is an Attenuated Mycobacterial Producer of Phosphorylated Nonpeptidic Antigens for Human γδ T Cells" *Infection and Immunity*, Dec. 1995, pp. 4628-4633, vol. 63, No. 12.
Behr, C. et al. "*Plasmodium Falciparum Stimuli for Human* γδ T Cells are Related to Phosphorylated Antigens of Mycobacterial" *Infection and Immunity*, Aug. 1996, pp. 2892-2896, vol. 64, No. 8.
Poccia, F. et al. "CD94/NKG2 Inhibitory Receptor Complex Modulates Both Anti-Viral and Anti-Tumoral Responses of Polyclonal Phosphoantigen-Reactive Vγ9Vδ2 T Lymphocytes" *The American Association of Immunologies*, 1997, pp. 6009-6017.
Fournie et al. Stimulation of γδ T Cells by Phosphoantigens, *66th Forum in Immunology*, May 1996, pp. 338-346.

(Continued)

*Primary Examiner*—Lawrence E Crane
(74) *Attorney, Agent, or Firm*—Saliwanchik, Lloyd & Saliwanchik

(57) ABSTRACT

The invention provides compounds comprising at least one phosphohalohydrin group of the formula:

$$X-CH_2-\underset{\underset{R1}{|}}{\overset{\overset{OH}{|}}{C}}-(CH_2)_n-O-\underset{\underset{O^-Cat^+}{|}}{\overset{\overset{O}{\|}}{P}}-O-\underset{\underset{O^-Cat^+}{|}}{\overset{\overset{O}{\|}}{P}}-O- \quad (1)$$

where X is a halogen selected from among I, Br, Cl,
R1 is selected from among —CH$_3$ and —CH$_2$—CH$_3$,
Cat+ is an organic or inorganic cation,
and n is an integer between 2 and 20,
processes for the production thereof and uses thereof, in particular therapeutic uses and for activating primate Tγ9δ2 lymphocytes.

33 Claims, 2 Drawing Sheets

OTHER PUBLICATIONS

Constant, P. et al. "Stimulation of Human γδ T Cells by Nonpeptidic Mycobacterial Ligands" *Science*, Apr. 8, 1994, pp. 267-270, vol. 264.

Poquet et al. "A Novel Nucleotide-Containing Antigen for Human Blood γδ T Lymphocytes" *Euro. J. Immunol.*, 1996, pp. 2344-2349, vol. 26.

Poquet, Y. et al. "High-Ph Anion-Exchange Chromatographic Analysis of Phosphorylated Compounds: Application to Isolation and Characterization of Nonpeptide Mycobacterial Antigens" *Analytical Biochemistry*, 1996, pp. 119-126, vol. 243.

Davisson, V.J. et al. "Phosphorylation of Isoprenoid Alcohols" *American Chemical Society, J. Org. Chem.*, 1986, pp. 4768-4779, vol. 51.

Davisson, V.J. et al. "Synthesis of Allylic and Momoallylic Isoprenoid Phyrophosphates" *J. American Chemical Society*, 1975, pp. 130-144, vol. 97, No. 7152.

Davisson, V.J. et al. "Synthesis of Nucleotide 5'-Diphosphates from 5'-O-Tosyl Nucleosides" *American Chemical Society, J. Org. Chem.*, 1987, pp. 1794-1801, vol. 52.

Knorre, D.G. et al. "General Method for the Synthesis of ATP Gamma-Derivatives" *FEBS Letters*, Nov. 1976, pp. 105-108, vol. 70, No. 1.

\* cited by examiner

PHOSPHOHALOHYDRINS, PROCESS FOR THE PRODUCTION THEREOF AND USE THEREOF

CROSS-REFERENCE TO RELATED APPLICATIONS

This application is a continuation of U.S. patent application Ser. No. 10/682,990, filed Oct. 14, 2003, now U.S. Patent No. 7,109,183, which is a divisional of U.S. patent application Ser. No. 09/786,054, filed on Mar. 1, 2001, now U.S. Patent No. 6,660,723, which is the national stage application of PCT International Application No. PCT/FR99/02058, filed on Aug. 27, 1999. The entire contents of each of the above-identified applications are hereby incorporated by reference.

This invention relates to novel phosphohalohydrins, to the process for the production thereof and to the use thereof for stimulating T$\gamma$9$\delta$2 lymphocytes bearing TCR receptors with V$\gamma$9 and V$\delta$2 variable regions.

In healthy individuals, the T$\gamma$$\delta$ lymphocytes of primates (humans, monkeys) present in the peripheral bloodstream usually constitute from 1 to 5% of the lymphocytes in the blood and play a role in the immune system. It has been demonstrated that they recognize their antigenic ligands by direct interaction with the antigen without presentation by molecules of the MHC by a presenting cell. T$\gamma$9$\delta$2 lymphocytes (sometimes also known as T$\gamma$2$\delta$2 lymphocytes) are T$\gamma$$\delta$ lymphocytes bearing TCR receptors with V$\gamma$9 and V$\delta$2 variable regions. They constitute the majority of T$\gamma$$\delta$ lymphocytes in human blood.

When activated, T$\gamma$$\delta$ lymphocytes exercise a strong cytotoxic activity which is unrestrained by the MHC and is particularly effective in killing various types of cells, in particular pathogenic cells. These may be cells infected by viruses ("$\gamma$$\delta$ T cell activation or anergy during infections: the role of nonpeptidic TCR ligands and HLA class I molecules" Fabrizio POCCIA et al, Journal of Leukocyte Biology, 62, 1997, p. 1-5), or by other intracellular parasites, such as mycobacteria ("The antituberculous *Mycobacterium bovis* BCG Vaccine is an attenuated Mycobacterial producer of phosphorylated nonpeptidic Antigens for human $\gamma$$\delta$ T cells" Patricia CONSTANT et al, Infection and Immunity, vol. 63, no. 12, December 1995, p. 4628-4633); or by protozoans ("*Plasmodium falciparum* stimuli for human $\gamma$$\delta$ T Cells are related to phosphorylated Antigens of mycobacteria" Charlotte BEHR et al, Infection and Immunity, Vol. 64, no. 8, 1996, p. 2892-2896). They may also be cancer cells ("CD94/NKG2 inhibitory receptor complex modulates both antiviral and antitumoral responses of polyclonal phosphoantigen-reactive V$\gamma$9 V$\delta$2 T lymphocytes" Fabrizio POCCIA et al, Journal of Immunology, 159, p. 6009-6015; "Stimulation of $\gamma$$\delta$ T cells by phosphoantigens" Jean-Jacques FOURNIE, Marc BONNEVILLE, Res. Immunol., 66$^{th}$ FORUM IN IMMUNOLOGY, 147, p. 338-347).

It has been demonstrated that, in the event of a mycobacterial infection, human T$\gamma$9$\delta$2 lymphocytes react to four natural, nonpeptidic molecules of a phosphorylated structure, known as phosphoantigens, which exhibit stimulation activity at a concentration of 1 to 5 nM (nanomolar) (WO-95/20673 and "Stimulation of human $\gamma$$\delta$ T cells by nonpeptidic Mycobacterial ligands" Patricia CONSTANT et al, Science, 264, p. 267-270).

These natural antigens have not been completely identified. Certain authors have erroneously presented them as alkene derivatives of pyrophosphate, in particular isopentenyl pyrophosphate IPP (U.S. Pat. No. 5,639,653 and "Natural and Synthetic nonpeptide antigens recognized by human $\gamma$$\delta$ T cells", Yoshimasa TANAKA et al, Nature, 375, 1995, p. 155-158). It has nonetheless now been demonstrated that none of these prenyl pyrophosphates is active at a concentration of nanomolar magnitude. The best results which have been obtained have been unable to demonstrate activity at below 3 $\mu$M for IPP and below 0.3 $\mu$M for dimethylallyl-UTP and 3-methyl-2-hexene pyrophosphate. The minimum active concentration of these compounds is thus, at best, of the order to 100 times higher than that of natural phosphoantigens.

With regard to IPP, it should in particular be noted that the most recent of the above-stated publications make the mistake of deducing the structure of the isopentenyl radical solely on the basis of mass spectrometry and the detection of a certain level of bioactivity. Indeed, apart from the fact that the compound analyzed in these publications was not purified and that a mass spectrum cannot identify uncharged species, it may be demonstrated that there are in fact several thousand different chemical structures which may have the same molecular weight and be a substituent of pyrophosphate in these molecules.

The fact that the minimum active concentration for IPP is much higher (some 1000 times higher) and that the intensity of the T$\gamma$9$\delta$2 lymphocyte responses obtained is much weaker than that for natural phosphoantigens demonstrates that IPP is not one of these natural phosphoantigens ("A novel nucleotide-containing antigen for human blood $\gamma$$\delta$ T lymphocytes", Y. Poquet et al, Eur. J. Immunol. 1996, 26, p. 2344-2349). This is moreover confirmed by numerous other observations: IPP is not found in sufficient concentration in mycobacterial extracts which stimulate T$\gamma$9$\delta$2 lymphocytes; according to "High pH anion exchange chromatographic analysis of phosphorylated compounds: application to isolation and characterization of non peptide mycobacterial antigens", Y. Poquet et al, Anal. Biochem, 243 no. 1, 1996, p. 119-126, IPP does not have the same chromatographic (HPAEC) characteristics as natural phosphoantigens; IPP and other natural isoprenoids are produced by all living cells, but these do not stimulate T$\gamma$9$\delta$2 lymphocytes.

Moreover, it is known that substances having bioactivity of the order of or greater than 1 $\mu$M are only rarely compatible with the economic constraints of operation on an industrial scale. The synthetic phosphoantigens which have hitherto been proposed thus cannot be processed on an industrial scale under acceptable economic conditions.

Natural phosphoantigens, on the other hand, may only be produced in very small quantities (WO 95/20673) and, since their precise chemical structure has still not yet been established, they cannot be synthesized. Economic industrial scale processing is thus likewise out of the question, despite their demonstrated great therapeutic worth.

The object of the invention is accordingly to provide novel chemical compounds which activate T$\gamma$9$\delta$2 lymphocytes at a minimum activation concentration of below 100 nM, in particular of the order of 1 nM.

A further object of the invention is to provide compounds which may be linked to a large number of organic groups, in particular to natural or synthetic peptide groups, so as to permit multifunctional compounds to be obtained.

A further object of the invention is to provide such compounds which may be synthesized simply, quantitatively and at low cost, i.e. in a manner compatible with the economic constraints of production on an industrial scale.

A further object of the invention is to provide an advantageous synthetic pathway for these compounds.

A further object of the invention is to provide a process for the production of the compounds according to the invention.

A further object of the invention is to suggest uses for the compounds according to the invention as a Tγ9δ2 lymphocyte activator and in particular therapeutic uses of the compounds according to the invention.

The invention accordingly provides compounds comprising at least one phosphohalohydrin group of the formula:

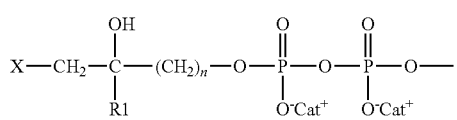
(1)

where X is a halogen selected from among iodine, bromine and chlorine,

R1 is selected from among —CH$_3$ and —CH$_2$—CH$_3$,

Cat$^+$ represents one or more organic or inorganic cation(s) (including the proton), which may be identical or different in the same compound, and n is an integer between 2 and 20.

A compound according to the invention may in particular comprise one or more phosphohalohydrin group(s) selected from among the esters of the following groups (IUPAC nomenclature) or among the compounds formed from these groups:

3-(halomethyl)-3-butanol-1-yl diphosphate, 3-(halomethyl)-3-pentanol-1-yl diphosphate, 4-(halomethyl)-4-pentanol-1-yl diphosphate, 4-(halomethyl)-4-hexanol-1-yl diphosphate, 5-(halomethyl)-5-hexanol-1-yl diphosphate, 5-(halomethyl)-4-heptanol-1-yl diphosphate, 6-(halomethyl)-6-heptanol-1-yl diphosphate, 6-(halomethyl)-6-octanol-1-yl diphosphate, 7-(halomethyl)-7-octanol-1-yl diphosphate, 7-(halomethyl)-7-nonanol-1-yl diphosphate, 8-(halomethyl)-8-nonanol-1-yl diphosphate, 8-(halomethyl)-8-decanol-1-yl diphosphate, 9-(halomethyl)-9-decanol-1-yl diphosphate, 9-(halomethyl)-9-undecanol-1-yl diphosphate, 10-(halomethyl)-10-undecanol-1-yl diphosphate, 10-(halomethyl)-10-dodecanol-1-yl diphosphate, 11-(halomethyl)-11-dodecanol-1-yl diphosphate, 11-(halomethyl)-11-tridecanol-1-yl diphosphate, 12-(halomethyl)-12-tridecanol-1-yl diphosphate, 12-(halomethyl)-12-tetradecanol-1-yl diphosphate, 13-(halomethyl)-13-tetradecanol-1-yl-diphosphate, 13-(halomethyl)-13-pentadecanol-1-yl diphosphate, 14-(halomethyl)-14-pentadecanol-1-yl diphosphate, 14-(halomethyl)-14-hexadecanol-1-yl diphosphate, 15-(halomethyl)-15-hexadecanol-1-yl diphosphate, 15-(halomethyl)-15-heptadecanol-1-yl diphosphate, 16-(halomethyl)-16-heptadecanol-1-yl diphosphate, 16-(halomethyl)-16-octadecanol-1-yl diphosphate, 17-(halomethyl)-17-octadecanol-1-yl diphosphate, 17-(halomethyl)-17-nonadecanol-1-yl diphosphate, 18-(halomethyl)-18-nonadecanol-1-yl diphosphate, 18-(halomethyl)-18-eicosanol-1-yl diphosphate, 19-(halomethyl)-19-eicosanol-1-yl diphosphate, 19-(halomethyl)-11-heneicosanol-1-yl diphosphate, 20-(halomethyl)-20-heneicosanol-1-yl diphosphate, 20-(halomethyl)-20-docosanol-1-yl diphosphate, 21-(halomethyl)-21-docosanol-1-yl diphosphate, 21-(halomethyl)-21-tricosanol-1-yl diphosphate.

The phosphohalohydrin compounds in accordance with one of the following formulae may be mentioned among the compounds according to the invention:

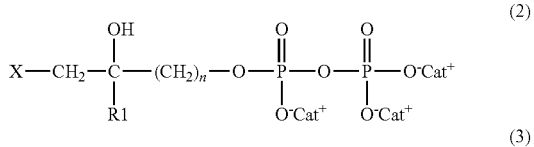
(2)

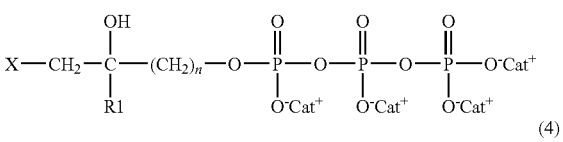
(3)

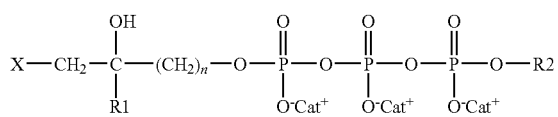
(4)

where R2 is an organic or inorganic substituent selected from among the group comprising:

substituents which do not prevent formation of the halohydrin function

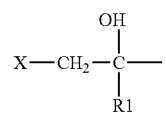

starting from the alkene function

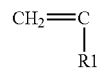

and halogen X$_2$ in the presence of water;

and substituents for which there is an R2—O—Y compound which is not reactive towards the halohydrin function of the compound of the formula:

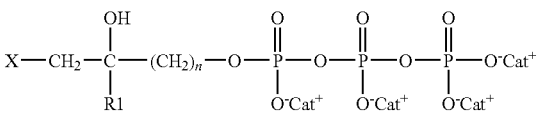
(3)

and selected such that R2—O—Y may react with the terminal phosphate of this compound (3) in order to obtain the compound (4).

Said compounds according to the invention are advantageously characterized in that n=2 and R1 is CH$_3$.

The compounds according to the invention advantageously additionally comprise at least one group selected from among the group comprising nucleoside derivatives, oligonucleotides, nucleic acids (RNA, DNA), amino acids, peptides, proteins, monosaccharides, oligosaccharides, polysaccharides, fatty acids, simple lipids, complex lipids, folic acid, tetrahydrofolic acid, phosphoric acids, inositol, vitamins, co-enzymes, flavonoids, aldehydes, epoxides and halohydrins.

In particular, the invention provides the phosphohalohydrin compounds of the formula (4) above in which R2 is selected from among the group comprising nucleoside derivatives, oligonucleotides, nucleic acids (RNA, DNA), amino acids, peptides, proteins, monosaccharides, oligosaccharides, polysaccharides, fatty acids, simple lipids, complex lipids, folic acid, tetrahydrofolic acid, phosphoric acids, inositol, vitamins, co-enzymes, flavonoids, phosphohalohydrins of the formula (1), aldehydes, epoxides and halohydrins.

The invention also provides compounds, the structure of which incorporates two or more groups of the formula (1), which may be identical or different, for example monomers, polymers, oligomers or dendrimers, or more generally molecules with two or more phosphorylated branches of the formula (1).

It should be noted that the compounds according to the invention are esters (monoesters or diesters) of phosphoric acid (this term encompassing those acids in which phosphorus is in oxidation state V, namely orthophosphoric acid, pyrophosphoric acid, metaphosphoric acid, triphosphoric acid, other polyphosphoric acids).

The invention provides a process for the production of the compounds according to the invention. According to the invention, halogen $X_2$ is reacted in the presence of water with a starting compound comprising at least one phosphorylated alkene group of the formula:

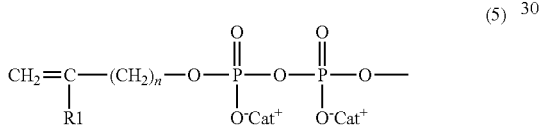

Advantageously and according to the invention, a salt formed from said starting compound is reacted in an aqueous or aqueous/alcoholic medium, at neutral pH, at a temperature of below 30° C., by mixing with an aqueous solution of the halogen $X_2$. Advantageously and according to the invention, the reaction is performed at atmospheric temperature at a temperature of between 0° C. and 25° C.

The starting compounds may themselves be obtained from alcohol:

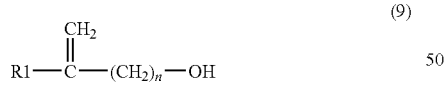

Advantageously and according to the invention, the starting compound is a salt of the formula:

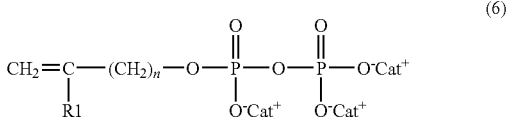

The pyrophosphohalohydrin compound of the formula (2) is then obtained.

An example of a complete reaction scheme for obtaining the compound (2) from the alcohol (9) is given below:

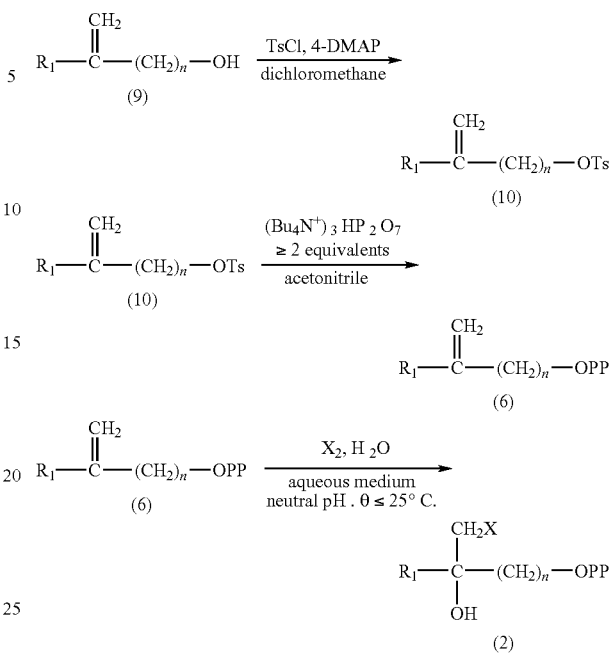

where TsCl is tosyl chloride,
4-DMAP is 4-dimethylaminopyridine,
$Bu_4 N+$ is tetrabutylammonium,
$(Bu_4N+)_3 HP_2O_7$ is tris(tetra n-butylammonium) hydrogenpyrophosphate,
PP represents the pyrophosphate group.

The reactions which allow compound (6) to be obtained from the alcohol (9) may be performed as described by: DAVISSON V. J. et. al. "Phosphorylation of Isoprenoid Alcohols" J. Org. Chem 1986, 51, 4768-4779, et DAVISSON V. J. et al. "Synthesis of Allylic and Homoallylic Isoprenoid Pyrophosphates" Methods in Enzymology, 1984, 110, 130-144.

Advantageously and according to the invention, the starting compound is a salt of the formula:

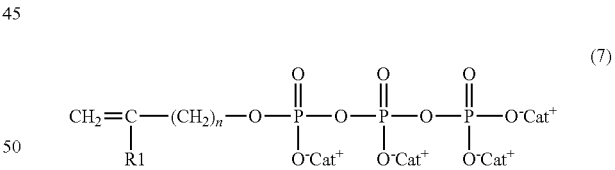

The triphosphohalohydrin compound of the formula (3) is then obtained.

An example of a complete reaction scheme for obtaining the compound (3) from the alcohol (9) is given below:

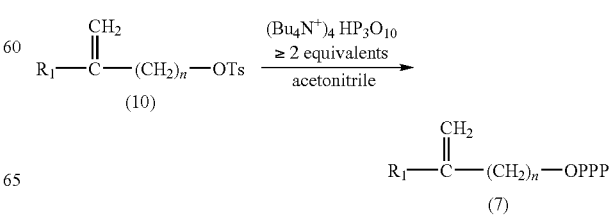

-continued

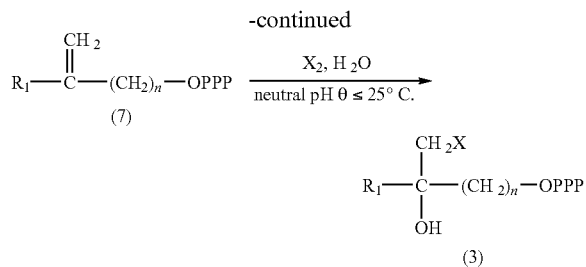

where PPP is the triphosphate group,
$(Bu_4N^+)_4HP_3O_{10}$ is tetralcis(tetra-n-butylammonium) hydrogentriphosphate.

The compound (10) is obtained from the alcohol (9) as stated above. The reaction which allows compound (7) to be obtained from the compound (10) may be performed under conditions similar to those described in the publications by DAVISSON V. J. et al or in DAVISSON V. J. et al "Synthesis of Nucleotide 5'-Diphosphates from (5'-O-Tosyl Nucleosides" J. Org. Chem. 1987, 52, 1794-1801.

Advantageously and according to the invention, in a first variant which allows a compound according to the invention of the formula (4) to be obtained, the above-stated production process according to the invention (reaction of $X_2$ in the presence of water with a phosphorylated alkene function) may be performed by using a salt of the following formula as the starting compound:

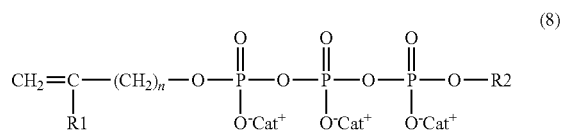

where R2 is an organic or inorganic substituent of a nature such as not to prevent formation of the halohydrin function

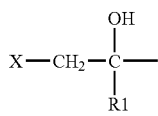

starting from the alkene function

and halogen $X_2$ in the presence of water.

The starting compound (8) may itself be prepared in accordance with one of the following reaction schemes:

- Reaction scheme 1:

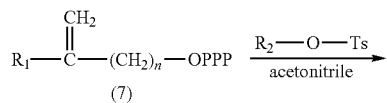

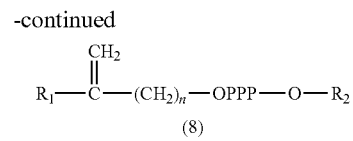

where Ts is tosyl.

The compound (7) may be obtained as stated above starting from the alcohol (9) and the intermediate compound (10). The reaction which allows compound (8) to be obtained from the compound (7) may be performed under conditions similar to those described in the publications by DAVISSON V. J. et al. This scheme may be used when R2—O-Ts is commercially available.

- Reaction scheme 2:

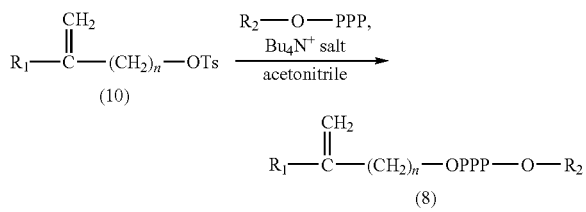

The intermediate compound (10) may be obtained as stated above starting from the alcohol (9). The reaction which allows compound (8) to be obtained from the compound (7) may be performed under conditions similar to those described in the publications by DAVISSON V. J. et al. This scheme may be used when R2—O—PPP is commercially available.

- Reaction scheme 3:

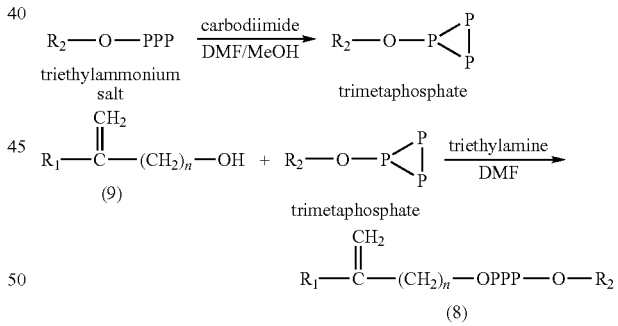

where DMF is dimethylformamide,
MeOH is methanol.

This reaction scheme 3 may be performed under conditions similar to those described in D. G. KNORRE et al "General method for the synthesis of ATP gamma derivatives" Febs letters, 1976, 70, 105-108.

This reaction scheme 3 cannot be used when R2 comprises a carbodiimide-reactive function (carboxylate, triphosphate etc.). It is, however, advantageous when R2—O—PPP is commercially available.

In the specific case where R2— is itself a halohydrin group of the formula:

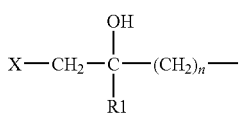

(12)

the following reaction scheme may be used:

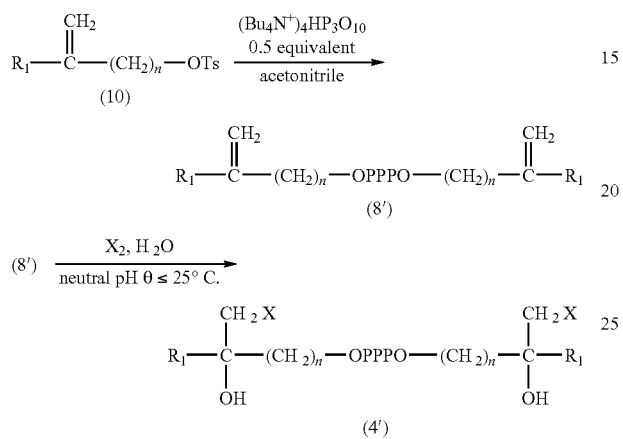

This compound (4') is a particular instance of the compound according to the invention of the formula (4).

It should be noted that, in all these reactions, acetonitrile may be replaced by any other aprotic dipolar solvent (dimethylformamide DMF, dimethyl sulfoxide DMSO etc.).

It should be noted that when preparing compounds (2), (3) and (4') and in the event that n≠2, the intermediate compound (10) may also be replaced by the chloride or bromide compound of the formula:

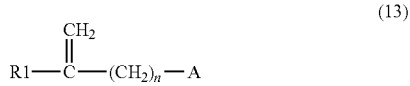

(13)

where A is chlorine or bromine.

The alcohols (9) are commercially available or may readily be obtained by a well known Grignard reaction between an alkenyl organomagnesium compound and formaldehyde or ethylene oxide.

In a second variant usable in certain cases, a compound of the formula (4) could be prepared by reacting the triphosphate compound according to the invention of the formula (3) starting from a salt soluble in an organic medium, such as a Bu$_4$N+ salt, in a subsequent stage with a compound R2—O—Y, where —O—Y is a leaving group and R2 is an organic or inorganic substituent selected such that R2—O—Y is capable of forming, by reaction with the compound (3), the compound according to the invention of the formula:

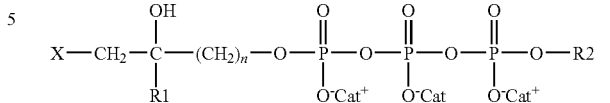

(4)

In order to be capable of forming the compound of the formula (4) in this manner, the compound R2—O—Y must in particular not be reactive towards the halohydrin function:

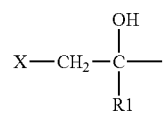

Moreover, R2—O—Y must react with the terminal phosphate of compound (3) to form the compound (4).

The reaction of the compound of the formula (3) with R2—O—Y is a nucleophilic substitution. This reaction is in particular possible and advantageous for R2 selected from among the group comprising alkyls and alkenes. Y is selected such that R2—O—Y may give rise to the compound (4) by nucleophilic substitution. Y is selected, for example, from among tosyl, brosyl and triflyl.

A compound according to the invention may accordingly be difunctional or multifunctional. The phosphohalohydrin function(s) bring(s) about a specific desired antigenic property towards Tγ9δ2 lymphocytes, and R2 or the other functional groups of the compound may exhibit other, in particular therapeutic, properties.

In the case of a compound according to the invention having two or more phosphohalohydrin groups of the formula (1), it is sufficient either to start from a starting compound having the corresponding number of phosphorylated alkene groups of the formula (5) and the corresponding chemical structure, or to use the compound of the formula (3) and to react it with an intermediate compound R2—O—Y having the corresponding number of —O—Y functions.

The invention also in particular relates to the novel phosphohalohydrin β ester compounds of the formula:

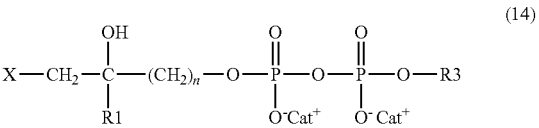

(14)

where X is a halogen selected from among iodine, bromine and chlorine,

R1 is selected from among —CH$_3$ and —CH$_2$—CH$_3$,

Cat$^+$ represents one or more organic or inorganic cation(s) (including the proton), which may be identical or different in the same compound, n is an integer between 2 and 20, R3— is selected from among:
  a halohydrin group of the formula (12),
  an epoxide group of the formula:

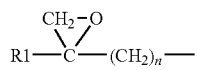

(15)

an alkene group of the formula:

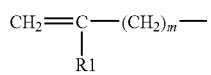

(16)

m being an integer between 1 and 20.

These compounds (14) are obtained by firstly performing the following initial step:

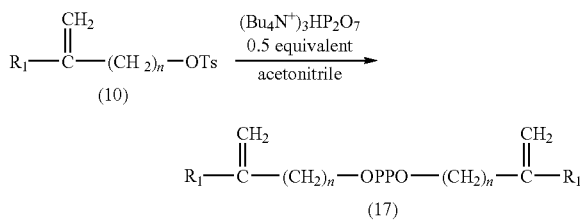

Then, the symmetrical diphosphodihalohydrin compound (14a) is obtained as follows:

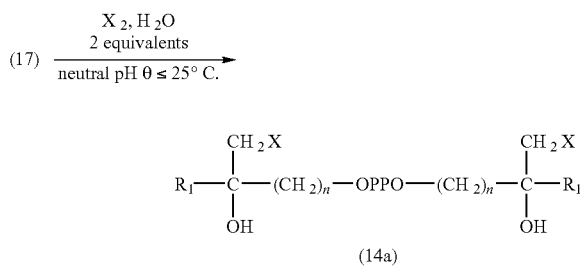

The asymmetrical α,β phosphodiester halohydrin/alkene compound (14b) is obtained as follows:

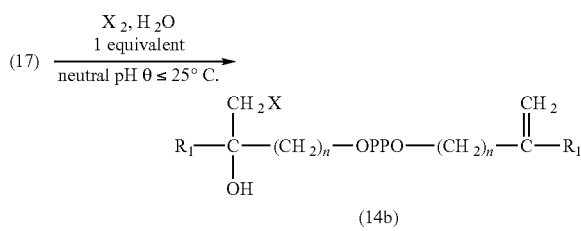

The asymmetrical α,β phosphodiester halohydrin/epoxide compound (14c) is obtained as follows:

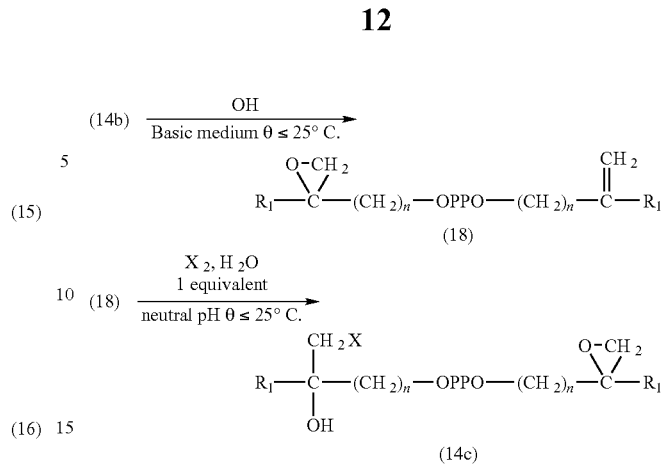

The invention also provides uses of the compounds according to the invention, in particular the compounds of the formula (2), as primate Tγ9δ2 lymphocyte activators, in particular to activate proliferation and/or cytotoxic activity and/or production of mediator substance(s) for primate Tγ9δ2 lymphocytes with TCR receptors comprising Vγ9 and Vδ2 variable regions.

The invention also provides uses of the compounds according to the invention for the treatment of cells sensitive to primate Tγ9δ2 lymphocytes in a natural or artificial medium which may contain Tγ9δ2 lymphocytes, in which medium said cells may be brought into contact with Tγ9δ2 lymphocytes and which is compatible with the compounds according to the invention (i.e. which is not likely to cause the breakdown thereof, at least under certain treatment conditions).

A "cell sensitive to Tγ9δ2 lymphocytes" is taken to mean any cell subject to the induced effector activity of the Tγ9δ2 lymphocytes: cell death (cell destruction by Tγ9δ2 lymphocytes); reception of cytokine released by Tγ9δ2 lymphocytes (TNF-α, INF-γ . . . ); possibly cellular proliferation induced by Tγ9δ2 lymphocytes.

The invention accordingly provides a Tγ9δ2 lymphocyte activation process, in particular a process for activating the proliferation of Tγ9δ2 lymphocytes and/or the cytotoxic activity of Tγ9δ2 lymphocytes and/or the production of mediator substance(s) by Tγ9δ2 lymphocytes, in which process these Tγ9δ2 lymphocytes are brought into contact with at least one compound according to the invention in a medium which contains Tγ9δ2 lymphocytes and is compatible with T lymphocyte growth. Advantageously and according to the invention, interleukin, in particular interleukin-2 (IL-2), is introduced into the medium in a proportion suitable to bring about lymphocyte growth in this medium. Indeed, the presence of the lymphocyte growth factor IL-2 is essential to achieve proliferation of the T lymphocytes, among which only the Tγ9δ2 lymphocytes have been activated by a compound according to the invention. This growth factor must thus be present in the medium for those uses in which proliferation of Tγ9δ2 lymphocytes is desired. This lymphocyte growth factor may pre-exist in the natural state or be induced or introduced into the medium, simultaneously or not with the incorporation of the compound according to the invention, in the same therapeutic composition or not. Nevertheless, in certain uses in which activation without proliferation of the Tγ9δ2 lymphocytes is desired (for example induced cytotoxicity), the presence of this growth factor is not helpful.

More specifically, the invention provides uses of the compounds according to the invention for therapeutic purposes for the curative or preventive treatment of pathological conditions producing cells sensitive to primate Tγ9δ2 lymphocytes in a medium which may contain these Tγ9δ2 lymphocytes and in which these cells may be brought into contact with the Tγ9δ2 lymphocytes.

Advantageously and according to the invention, at least one compound according to the invention is used at a concentration in the medium which brings about activation of polyclonal proliferation of Tγ9δ2 lymphocytes. This medium may be selected from among human blood, non-human primate blood, human blood extracts, non-human primate blood extracts.

Said medium may be extracorporeal, said activation process according to the invention then being an extracorporeal cellular treatment, in particular applicable in a laboratory, for studying Tγ9δ2 lymphocytes or the properties thereof, or for diagnostic purposes. The invention also provides a composition for extracorporeal (ex vivo) diagnostics, wherein it comprises at least one compound according to the invention.

Said medium may also be intracorporeal, activation of the Tγ2δ2 lymphocytes then being of therapeutic use.

More particularly, said medium is the peripheral bloodstream of a primate. The invention accordingly in particular provides a process for the activation of Tγ9δ2 lymphocytes in the peripheral bloodstream of a primate, in particular humans, into which is administered at least one compound according to the invention in a quantity suitable for activating Tγ9δ2 lymphocytes. At least one compound according to the invention is thus administered by a general route, in particular parenterally into the peripheral bloodstream.

Said medium may also comprise a cellular site to be treated and at least one compound according to the invention is administered directly in contact with the cellular site to be treated (topical administration).

The invention accordingly in particular provides therapeutic uses of the compounds according to the invention for treating pathological conditions in primates, said conditions belonging to the group comprising cancers, infectious diseases, in particular mycobacterial infections (leprosy, tuberculosis etc.); parasitic conditions (malaria etc.); pathological immunodeficiency syndromes (AIDS etc.). According to the invention, a therapeutic composition is administered which is suitable for releasing into the peripheral bloodstream and/or at a cellular site to be treated a quantity of at least one compound according to the invention capable of activating Tγ9δ2 lymphocytes. Indeed, it has been demonstrated in general terms in the above-stated prior art that a composition having the property of activating Tγ9δ2 lymphocytes may advantageously be used for treating these pathological conditions.

As is conventional, throughout the text the terms "therapy" or "therapeutic" encompass not only curative treatment or care, but also preventive treatment (prophylaxis), such as vaccination, together with intracorporeal diagnostics (administration for diagnostic purposes). Indeed, by permitting activation of Tγ9δ2 lymphocytes, the invention allows immunostimulatory treatments which may be advantageous not only prophylactically by preventing the development of pathogenic cells sensitive to Tγ9δ2 lymphocytes, but also curatively by inducing destruction of pathogenic cells sensitive to Tγ9δ2 lymphocytes.

The invention accordingly provides a therapeutic composition comprising at least one compound according to the invention. More specifically, the invention relates to a therapeutic composition comprising a quantity capable of being administered to a primate, in particular in contact with the peripheral bloodstream or topically, of at least one compound according to the invention, in particular for the preventive or curative treatment of the above-stated pathological conditions. A composition according to the invention may be an immunostimulant composition or a vaccine, the compounds according to the invention being antigens which activate Tγ9δ2 lymphocytes.

Advantageously and according to the invention, the therapeutic composition is characterized in that it moreover comprises a proportion of interleukin, in particular interleukin-2, suitable for bringing about lymphocyte growth in the medium into which it is to be administered.

A therapeutic composition according to the invention may be prepared in a dosage form capable of being administered by a general route, in particular parenterally directly into the peripheral bloodstream of a primate, with at least one compound according to the invention in a quantity suitable to activate Tγ9δ2 lymphocytes and one or more appropriate excipient(s). Given the very low active concentration of the compounds according to the invention (of the order of 0.1 to 10 nM), such administration may be made without risk of toxicity.

A therapeutic composition according to the invention may also be prepared in a dosage form appropriate for topical administration, directly in contact with the cells sensitive to Tγ9δ2 lymphocytes.

The dosage form of a therapeutic composition according to the invention is produced in accordance with the selected route of administration using conventional pharmaceutical formulation methods. The quantity and concentration of compound(s) according to the invention and the dosage are determined by reference to known chemotherapeutic methods for the diseases to be treated, taking account of the bioactivity of the compounds according to the invention towards Tγ9δ2 lymphocytes, the individual to be treated, the disease in question and the desired biological effects.

Advantageously and according to the invention, in the case of a bioactive compound at a concentration of between 1 nM and 10 nM, the quantity of compound(s) according to the invention administered by a general route is between 0.1 μg and 100 μg, in particular between 1 μg and 10 μg, per kilogram of patient body weight.

It has moreover been demonstrated in vitro that the compounds according to the invention exhibit no general toxicity even at concentrations of up to 100 μM, i.e. of the order of $10^5$ times the bioactive concentration. Furthermore, it is known that the biochemical class of molecules to which the compounds according to the invention belong (phosphoesters) comprises a family of metabolic compounds found in any living cell. The compounds according to the invention thus exhibit no toxic effects other than those induced by the bioactivity thereof upon Tγ9δ2 lymphocytes.

Moreover, certain compounds according to the invention have a sufficiently low molecular weight (in particular below 500) to be compatible with the elimination thereof via the kidneys and urine.

One example formulation of an injectable therapeutic composition according to the invention for a primate weighing 1 kg is as follows: 5 μg of 3-(iodomethyl)-3-butanol-1-yl diphosphate (IHPP) diluted in 0.5 ml of sterile phosphate buffer at pH 7 and adjusted to 37° C.

In this manner, 5 μg of IHPP (compound of the formula (2)) are administered per 1 kg of animal body weight, corresponding to a concentration in the circulating blood such as to be greater than the bioactive concentration of IHPP (a concentration of 10 nM of IHPP corresponding to approx. 5 ng/ml).

It should be noted that the majority of the excipients or other conventionally used pharmaceutically acceptable additives are chemically compatible with the compounds according to the invention.

A therapeutic composition according to the invention may also advantageously comprise one or more other active ingredient(s), in particular to bring about a synergistic effect. In particular, a compound according to the invention may act as a vaccine adjuvant. The therapeutic vaccine composition according to the invention then comprises a known vaccine composition to which is added a quantity of compound(s) according to the invention capable of activating the Tγ9δ2 lymphocytes which will not only be able to exert their anti-infective activity directly, but will also be able to activate the T lymphocytes which effect the conventional vaccine response.

A therapeutic composition according to the invention may also itself incorporate primate Tγ9δ2 lymphocytes in a culture in a medium compatible with T lymphocyte growth. It may then be used for treating primates, or more generally vertebrates with which administration of primate Tγ9δ2 lymphocytes may be performed under conditions of immune compatibility towards said primate Tγ9δ2 lymphocytes. Such a composition according to the invention may be administered by a general route, or even by a topical route, in contact with target pathogenic cells, sensitive to said primate Tγ9δ2 lymphocytes.

The invention also provides the use of at least one compound according to the invention for the production of a therapeutic composition according to the invention. More particularly, the invention relates to the use of at least one compound according to the invention for the production of a therapeutic composition intended for the preventive or curative treatment of a pathological condition of humans or vertebrates which produces cells sensitive to primate Tγ9δ2 lymphocytes, in particular a pathological condition selected from the group comprising cancers, infectious diseases, parasitic conditions and pathological immunodeficiency syndromes. To this end, the invention also provides the use of at least one compound according to the invention for the production of a therapeutic composition intended to be administered, in particular in contact with the peripheral bloodstream or by a topical route, to a primate, in particular to humans, for the preventive, or curative treatment of a pathological condition as mentioned above.

The invention also provides a process for the production of a composition, in particular a therapeutic composition, according to the invention having the characteristic of activating Tγ9δ2 lymphocytes, in which process at least one compound according to the invention is used.

The invention also relates to a process for the production of a therapeutic composition intended for the preventive or curative treatment of a pathological condition of humans or vertebrates which produces cells sensitive to primate Tγ9δ2 lymphocytes, in which process at least one compound according to the invention is used. The invention in particular relates to a process for the production of a therapeutic composition intended to be administered, in particular in contact with the peripheral bloodstream or by a topical route, to a primate, for the preventive or curative treatment of a pathological condition which produces cells sensitive to Tγ9δ2 lymphocytes, in particular a pathological condition belonging to the group stated above, in which process at least one compound according to the invention is used.

Advantageously and according to the invention, in a production process according to the invention, at least one compound according to the invention is brought into contact with a medium which contains primate Tγ9δ2 lymphocytes, and is compatible with T lymphocyte growth, in a quantity suitable to activate these Tγ9δ2 lymphocytes in this medium. Advantageously and according to the invention, said medium comprises a substance selected from among primate blood and primate blood extracts. A therapeutic composition containing activated Tγ9δ2 lymphocytes is then obtained so allowing a cellular therapeutic approach to be performed.

It should be noted that the compounds according to the invention are halogenated and, for this reason alone, cannot correspond to natural phosphoantigens, in particular to the molecules known as Tubag1, Tubag2, Tubag3 and Tubag4 obtained as described in WO 95/20673. It is in any event possible to demonstrate for example that these natural phosphoantigens are broken down by the bromine water used for the chemical production of the phosphobromohydrins according to the invention. The compounds according to the invention are thus not natural antigens, but are synthetic antigens which activate Tγ9δ2 lymphocytes at concentrations of the same order and with an efficiency similar to or even greater than that of natural antigens.

It should also be noted that, contrary to the prior art as illustrated by U.S. Pat. No. 5,639,653, which considered that the presence of an alkyl or alkene group was essential to activate human Tγ9δ2 lymphocytes, the inventors have observed that by destroying the alkene bond with the addition of halogen, an element absent from natural biological compounds, the Tγ9δ2 lymphocytes are activated extremely strongly and at very low concentration. In particular, it may be observed that the effect may even exceed that of phosphoantigens of natural origin.

Further features, objects and advantages of the invention will be evident from the following Examples, which are provided in non-limitative manner merely for purposes of explanation, and from the figures.

EXAMPLE 1

Production of 3-(bromomethyl)-3-butanol-1-yl diphosphate (BrHPP)

Figure 1:
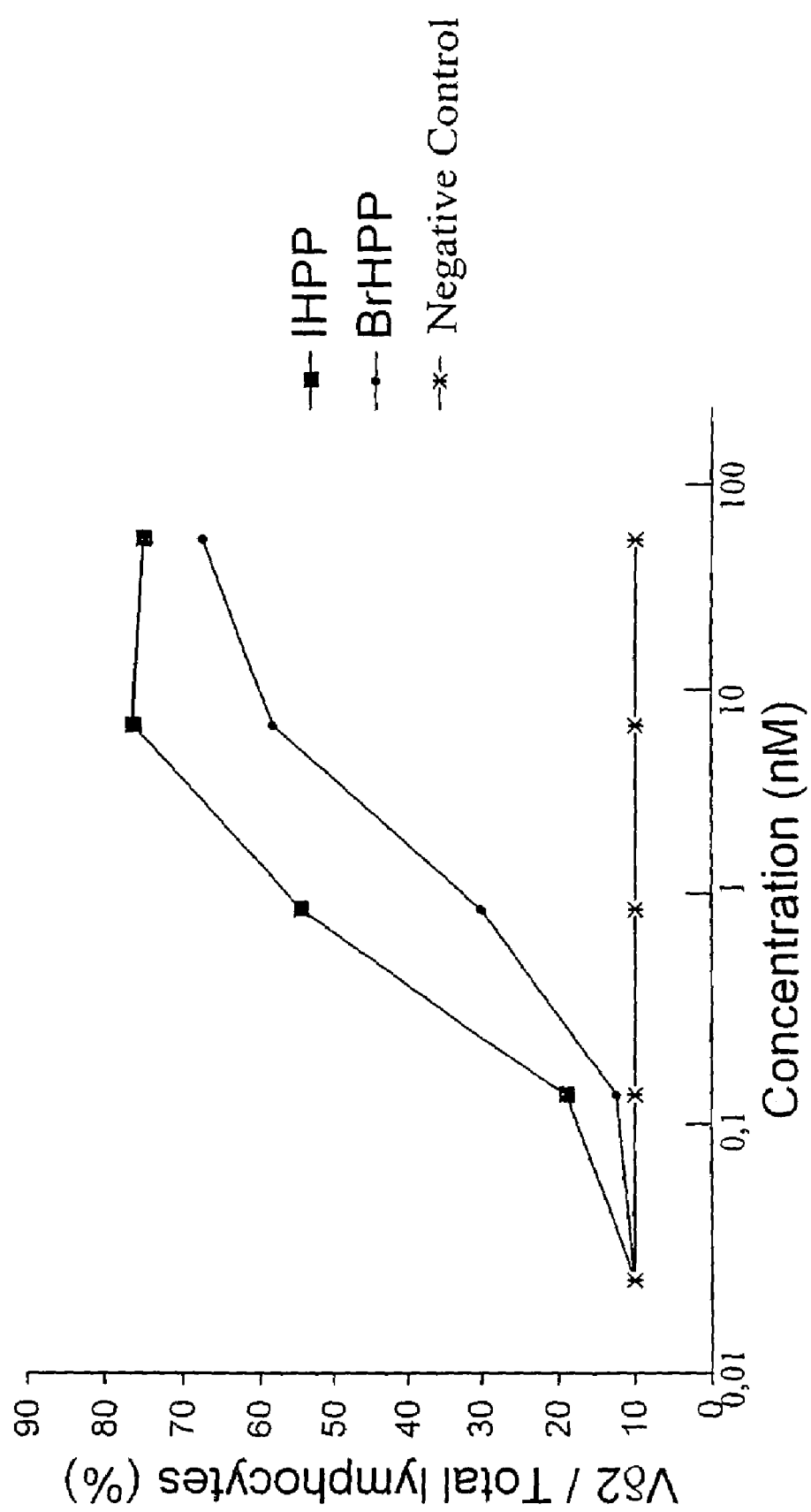
FIG. 1 is a graph showing the results obtained in Example 10.

Preparation of 3-methyl-3-butene-1-yl tosylate (isopentenyl tosylate):

2.32 mmol (442 mg) of tosyl chloride and 2.55 mmol (312 mg) of 4-(N,N-dimethylamino)pyridine are introduced while stirring with a magnetic stirrer into 5 ml of anhydrous dichloromethane in a glass reaction vessel which is equipped for handling under an inert atmosphere and has been carefully dried. 2.32 mmol (200 mg) of isopentenol dissolved in approx. 1 ml of dichloromethane are slowly added to this mixture through a septum using a syringe. The reaction is monitored by thin-layer chromatography on silica (silica gel 60 F-254; eluent: pentane/ethyl acetate 85/15 vol./vol.; $R_f$ (product)=0.4 and $R_f$ (TsCl)=0.5). After approx. 3 hours' stirring under a nitrogen atmosphere, the reaction mixture is diluted in a large volume of hexane (approx. 100 ml), resulting in the immediate formation of a white precipitate. The mixture is then filtered and the filtrate concentrated by evaporation under reduced pressure. The solution is then diluted with diethyl ether and refiltered. Once the solvent has evaporated, a yellowish oil is obtained. The product is purified by preparative chromatography through a silica column (silica gel 60; eluent: pentane/ethyl acetate 85/15). In this manner, 1.98 mmol (475 mg) of 3-methyl-3-butene-1-yl tosylate (85% isolated yield) are obtained. The compound (colorless oil) is stored at +4° C. in an anhydrous medium.

Preparation of tris(tetra-n-butylammonium) hydrogenpyrophosphate:

4.5 mmol (1 g) of dihydrogenpyrophosphate disodium salt ($Na_2H_2P_2O_7$) are dissolved in 10 ml of cold deionized water which has previously been adjusted to pH 9 with a 10 mM ammonia solution. The solution is passed through a column containing 19 milliequivalents (4 g) of DOWEX® 50-WX8-200 cationic resin ($H^+$ form). The acid solution is eluted with 15-20 ml of cold deionized water at pH 9. The collected solution is immediately titrated at pH 7.3 using a 40% aqueous solution of tetra-n-butylammonium hydroxide ($Bu_4NOH$). After freeze-drying, 4 g of tetra-n-butylanrrnonium salt are obtained as a hygroscopic white solid. The salt is dissolved in 10 ml of anhydrous acetontrile. The solution is subsequently filtered, then dried by evaporation of the solvent under reduced pressure in successive stages. In this manner, a solution of tris(tetra-n-butylammonium) hydrogenpyrophosphate is obtained with a purity of 98% (result deduced from analysis by ionic chromatography (HPAEC)). The volume is adjusted to achieve a salt concentration of between 0.5 and 1 M. The solution is stored at −20° C. in an anhydrous medium.

Preparation of 3-methyl-3-butene-1-yl diphosphate (isopentenyl pyrophosphate):

2.5 ml of a solution of tris(tetra-n-butylammonium) hydrogenpyrophosphate at a concentration of 0.7 M (1.75 mmol) in anhydrous acetonitrile are introduced into a glass reactor which has been dried carefully. The reactor is cooled with an ice bath, then 0.70 mmol (168 mg) of 3-methyl-3-butene-1-yl tosylate dissolved in a minimum quantity of acetonitrile (0.5-1 M) are added using a syringe, while stirring with a magnetic stirrer. Once the tosylate has been introduced, the ice bath is removed, then the reaction is allowed to continue at room temperature with stirring. The progress of the reaction is then monitored by ionic chromatography (HPAEC). After approx. 3 hours, the solvent is evaporated under reduced pressure and the reaction medium redissolved in 3 ml of a 98/2 (vol./vol.) water/2-propanol mixture. The solution is passed through a column containing 19 milliequivalents (4 g) of DOWEX® 50-WX8-200 cationic resin ($NH_4^+$ form), then eluted with 10 ml of the water (pH 9)/2-propanol 98/2 (vol./vol.) mixture. After freeze-drying, a white solid containing the crude product is collected.

Purification:

The pyrophosphate and the traces of ammonium monophosphate are separated from the medium by coprecipitation in the presence of ammonium hydrogencarbonate. The crude product obtained in the preceding stage is dissolved in 4 ml of 0.1 M ammonium hydrogencarbonate, which is transferred into a 25 ml centrifuge tube. The solution is then treated with 10 ml of a 1/1 (vol./vol.) acetonitrile/2-propanol mixture by shaling the mixture vigorously (vortex) for a few minutes until a white precipitate has formed. The tube is then centrifuged at 2000 rpm at 10° C. for 5 minutes. The supernatant, into which the organic salts have been extracted, is stored at +4° C. The procedure is repeated by redissolving the precipitate in 3 ml of 0.1 M amrnonium hydrogencarbonate, to which 7 ml of the acetonitrile/2-propanol mixture are added. The two supernatants are combined and the solvent evaporated under a vacuum. An oily liquid is obtained which is stored at +4° C.

The ammonium tosylate is separated from the reaction medium by extraction with the 1/1 (vol./vol.) chloroform/methanol solvent. The oily liquid from the preceding stage is dissolved in 4 ml of water at pH 9 and treated with 1 ml of this solvent by a conventional extraction procedure which is repeated 3 times. Any traces of solvent are then removed from the aqueous phase by evaporation under reduced pressure at 30° C. On the basis of analysis by ionic chromatography (HPAEC), an 83% yield of 3-methyl-3-butene-1-yl diphosphate (0.58 mmol, 172 mg) is obtained. The solution is stored at −20° C.

The product is then purified in accordance with requirements by anion exchange chromatography through 360 mg to 10 g Sep-Pak Accell Plus QMA (Waters®) cartridges eluted in succession respectively by 20 mM, 40 mM, 100 mM then 200 mM aqueous ammonium hydrogencarbonate solutions, with the eluted fractions being monitored by chromatography (HPAEC). The fractions corresponding to the purified product are combined and then freeze-dried.

Preparation of 3-(bromomethyl)-3-butanol-1-yl diphosphate:

0.34 mmol (100 mg) of isopentenyl pyrophosphate (ammonium salt) dissolved in 2 ml of neutral pH deionized water are treated under a fume hood at room temperature with 1.9 ml (0.34 mmol) of bromine in a saturated aqueous solution (0.18 M). The bromine solution is added gradually and preferably to a cold solution of the ammonium salt, with the mixture being stirred periodically until the bromine water has become colorless. In the event that bromine is added in a slight excess (persistent yellow color), the solution is transferred into a glass flask and then exposed to reduced pressure (rotary evaporator) for a few minutes at a temperature of 30° C. until the color disappears. The product 3-(bromomethyl)-3-butanol-1-yl diphosphate is produced quantitatively (0.33 mmol, 130 mg); this result being deduced from analysis by ionic chromatography (HPAEC). For the purpose of performing biological testing, the resultant aqueous solutions are filtered and then neutralized by being passed through a cationic resin column. The bromide ions may be removed from the solution using a DIONEX® apparatus comprising an OnGuard®-Ag cartridge attached to an OnGuard®-H cartridge. This apparatus allows selective retention of the halide ions from the solution. For the purpose of performing biological testing, the aqueous solutions of the product are sterilized by filtration through a 0.2 µm filter and stored (preferably with a neutral to slightly acidic pH) at −20° C. In the case of testing performed in vivo, the solutions are passed beforehand through a DOWEX® 50-WX8-200 cationic resin column ($Na^+$ form) eluted by two column volumes of deionized water.

EXAMPLE 2

Production of 3-(iodomethyl)-3-butanol-1-yl diphosphate (IHPP)

Preparation of Iodized Water:

A solution of iodized water of the order of 0.5 to 1 mM is prepared by extended sonication (approx. 15 minutes) of a few crystals of iodine in a solution of deionized water and filtration. For tests involving larger quantities, solutions having a higher iodine concentration may be obtained by adding a small proportion of alcohol to the initial aqueous solution. The iodized water is then titrated with sodium thiosulfate using starch solution as a color indicator.

Preparation of 3-(iodomethyl)-3-butanol-1-yl diphosphate:

One micromole (1 ml of a millimolar solution) of isopentenyl pyrophosphate prepared according to Example 1 in the form of the ammonium salt in an aqueous or aqueous/alcohol medium of neutral pH is treated at room temperature by addition of one micromole of iodine in an aqueous solution (1.43 ml of 0.7 mM iodized water). The solution is left for 30 minutes at room temperature, then for 30 minutes at +4° C. while periodically being stirred vigorously. Once the iodized water has become colorless, the product 3-(iodomethyl)-3-butanol-1-yl diphosphate is produced quantitatively (I micromole in approx. 2.5 ml). The solution is then treated as in Example 1 for the performance of biological testing and/or for the performance of in vivo testing and stored at −20° C.

EXAMPLE 3

Production of 3-(chloromethyl)-3-butano-1-1-yl diphosphate (C1HPP)

Preparation of Chlorine Water:
The solution of chlorine water is prepared by bubbling gaseous chlorine through a solution of deionized water. The solution is then titrated with sodium thiosulfate in the presence of excess potassium iodide and using starch solution as a color indicator.

Preparation of 3-(chloromethyl)-3-butanol-1-yl diphosphate:
One micromole (1 ml of a millimolar solution) of isopentenyl pyrophosphate prepared according to Example 1 in the form of the ammonium salt in an aqueous or aqueous/alcohol medium of neutral pH is treated at room temperature by addition of one micromole of chlorine in an aqueous solution (72 µl of 14 mM chlorine water). After 30 minutes at room temperature with periodic stirring, the product 3-(chloromethyl)-3-butanol-1-yl diphosphate is produced quantitatively (in this case 1 micromole in approx. 1.1 ml). The solution is then treated as in Example 1 for the performance of biological testing and/or for the performance of in vivo testing and stored at −20° C.

EXAMPLE 4

Production of 3-(bromomethyl)-3-butanol-1-yl triphosphate (BrHPPP)

Preparation of tetrakis(tetra-n-butylammonium) hydrogentriphosphate:
2.1 mmol (1 g) of tripolyphosphate hexahydrate pentasodium salt ($Na_5P_3O_{10}.6H_2O$) are dissolved in 10 ml of cold deionized water which has previously been adjusted to pH 9 with a 10 mM ammonia solution. The solution is passed through a column containing 21 milliequivalents (4.4 g) of DOWEX® 50-WX8 cationic resin ($H^+$ form). The acid solution is eluted with 20-25 ml of cold deionized water at pH 9. The collected solution is immediately titrated at pH 7.0 using a 40% aqueous solution of tetra-n-butylammonium hydroxide ($Bu_4NOH$). After freeze-drying, 2.5 g of tetra-n-butylammonium salt are obtained as a hygroscopic white solid. The salt is dissolved in 10 ml of anhydrous acetonitrile. The solution is subsequently filtered, then dried by evaporation of the solvent under reduced pressure in successive stages. In this manner, a solution of tetrakis(tetra-n-butylamnrnonium) hydrogentriphosphate with a purity of 95% is obtained (result deduced from analysis by ionic chromatography (HPAEC)). The volume is adjusted to achieve a salt concentration of between 0.5 and 1 M. The solution is stored at −20° C. in an anhydrous medium.

Preparation of 3-methyl-3-butene-1-yl triphosphate (isopentenyl triphosphate):
Using the procedure described for the preparation of 3-methyl-3-butene-1-yl diphosphate (Example 1), 2 mmol of a molar solution of tetralcis(tetra-n-butylammonium) hydrogentriphosphate are reacted under a nitrogen atmosphere with 1 mmol (240 mg) of 3-methyl-3-butene-1-yl tosylate prepared according to Example 1 in 4 ml of anhydrous acetonitrile for 24 hours. By using a precipitation/extraction purification procedure similar to that applied to 3-methyl-3-butene-1-yl diphosphate, on the basis of analysis by ionic chromatography (HPAEC), a yield of 74% of 3-methyl-3-butene-1-yl triphosphate (0.74 mmol, 292 mg) is obtained. Phosphohalohydrin compounds according to the invention are prepared for the purpose of biological testing by using a fraction of the product obtained at this stage which is purified by HPAEC through an IonPac® AS11 column, with two or more chromatographic passes being combined. In this manner, approx. 2 ml of an aqueous millimolar solution of neutral pH of 3-methyl-3-butene-1-yl triphosphate are prepared in the form of an ammonium salt.

Preparation of 3-(bromomethyl)-3-butanol-1-yl triphosphate:
300 nmol (300 µl of a millimolar solution) of isopentenyl triphosphate are treated at room temperature by addition of 300 nmol of bromine in a saturated aqueous solution (1.7 µl of 180 mM bromine water). The color of the bromine water disappears virtually instantaneously. Once the mixture has been stirred and the bromine has become colorless (virtually instantaneously), the product 3-(bromomethyl)-3-butanol-1-yl triphosphate is produced quantitatively (300 µl of a millimolar solution). The solution is then treated as in Example 1 for the performance of biological testing and/or for the performance of in vivo testing and stored at −20° C.

EXAMPLE 5

Production of 3-(iodomethyl)-3-butanol-1-yl diphosphate (IHPPP)

300 mmol (300 µl of a millimolar solution) of isopentenyl triphosphate prepared according to Example 4 are treated in an aqueous or aqueous/alcohol medium of neutral pH by addition of 429 µof 0.7 mM iodized water prepared according to Example 2. The solution is left for 30 minutes at room temperature while periodically being stirred vigorously. Once the iodized water has become colorless, the product 3-(iodomethyl)-3-butanol-1-yl triphosphate is produced quantitatively (729 µl of a 411 µM solution). The solution is then treated as in Example 1 for the performance of biological testing and/or for the performance of in vivo testing and stored at −20° C.

EXAMPLE 6

Production of α,γ di-[3-(bromomethyl)-3-butanol-1-yl] triphosphate (diBrHTP)

Preparation of α,γ di-[3-methyl-3-butene-1-yl] triphosphate:
Using the procedure described for the preparation of 3-methyl-3-butene-1-yl diphosphate (Example 1), 0.5 mmol of a molar solution of tetrakis(tetra-n-butylammonium) hydrogentriphosphate (prepared according to Example 4) are reacted under a nitrogen atmosphere with 1 mmol (240 mg) of 3-methyl-3-butene-1-yl tosylate (prepared according to Example 1) in 4 ml of anhlydrous acetonitrile for 24 hours. By using a precipitation/extraction purification procedure similar to that applied to 3-methyl-3-butene-1-yl diphosphate, on the basis of analysis by ionic chromatography (HPAEC), a yield of 81% of α,γ di-[3-methyl-3-butene-1-yl] triphosphate (0.4 mmol, 178 mg) is obtained. Phosphohalohydrin compounds according to the invention are prepared for the purpose of biological testing by using a fraction of the product obtained at this stage which is purified by HPAEC through an Ionpac® AS11 column, with two or more chromatographic passes being combined. Before each chromatographic pass and in order to improve isolation of the product, the fraction to be purified is treated enzymatically with alkaline phosphatase in order to break down the isopentenyl triphosphate which is a secondary product of the reaction. In this manner, approx. 1 ml of an aqueous millimolar solution of neutral pH of α,γ di-[3-methyl-3-butene-1-yl] triphosphate are prepared in the form of an ammonium salt.

Preparation of α,γ di-[3-(bromomethyl)-3-butanol-1-yl] triphosphate:

250 nmol (250 μl of a millimolar solution) of α,γ di-[3-methyl-3-butene-1-yl] triphosphate are treated at room temperature by addition of 250 nmol of bromine in a saturated aqueous solution (1.4 μl of 180 mM bromine water). Once the mixture has been stirred and the bromine has become colorless (virtually instantaneously), the product α,γ di-[3-(bromomethyl)-3-butanol-1-yl] triphosphate is produced quantitatively (approx. 250 μl of a millimolar solution). The solution is then treated as in Example 1 for the performance of biological testing and/or for the performance of in vivo testing and stored at −20° C.

EXAMPLE 7

Production of α,γ di-[3-(iodomethyl)-3-butanol-1-yl] triphosphate (diIHTP)

250 nmol (250 μl of a millimolar solution) of α,γ di-[3-methyl-3-butene-1-yl] triphosphate prepared according to Example 6 are treated in an aqueous or aqueous/alcohol medium of neutral pH by addition of 358 μl of 0.7 mM iodized water prepared according to Example 2. The solution is left for 30 minutes at room temperature while periodically being stirred vigorously. Once the iodized water has become colorless, the product α,γ di-[3-(iodomethyl)-3-butanol-1-yl] triphosphate is produced quantitatively (608 μl of a 411 μM solution). The solution is then treated as in Example 1 for the performance of biological testing and/or for the performance of in vivo testing and stored at −20° C.

EXAMPLE 8

Production of Uridine 5'-triphosphate γ-[3-(iodomethyl)-3-butanol-1-yl]

Preparation of Uridine 5'-triphosphate γ-[3-methyl-3-butene-1-yl]:

This product is prepared in accordance with the procedure described by KNORRE D. C. et al. "General Method for the synthesis of ATP Gamma-derivatives" Febs Letters, 1976, 70-1, 105-108, starting from 40 μmol of uridine 5'-triphosphate (UTP) (triethylammonium salt) in the presence of an excess of isopentenol. Phosphohalohydrin compounds according to the invention are prepared for the purpose of biological testing by purifying a fraction of the product obtained by HPAEC through an IonPac®) AS11 column, with two or more chromatographic passes being combined. Before each chromatographic pass and in order to improve isolation of the product, the fraction to be purified is treated enzymatically with alkaline phosphatase in order to break down the secondary products (UDP and UMP) and unreacted UTP. In this manner, approx. 500 μl of an aqueous 300 μM solution of neutral pH of uridine 5'-triphosphate γ-[3-methyl-3-butene-1-yl] are prepared in the form of an ammonium salt.

Preparation of Uridine 5'-triphosphate γ-[3-(iodomethyl)-3-butanol-1-yl]:

75 nmol (250 μl of a 300 μM solution) of uridine 5'-triphosphate γ-[3-methyl-3-butene-1-yl] in ammonium salt form are treated in an aqueous medium of neutral pH by addition of 108 μl of 0.7 mM iodized water prepared according to Example 2. The solution is left for 20 minutes at room temperature while periodically being stirred vigorously. Once the iodized water has become colorless, the product uridine 5'-triphosphate γ-[3-(iodomethyl)-3-butanol-1-yl] is produced quantitatively (approx. 360 μl of a 200 μM solution). The solution is then treated as in Example 1 for the performance of biological testing and/or for the performance of in vivo testing and stored at −20° C.

EXAMPLE 9

Production of α,β, di[3-bromomethyl-3-butanol-1-yl] diphosphate

This product is prepared in accordance with a procedure analogous to that described in Example 6, with tetrakis(tetra-n-butylammonium) hydrogentriphosphate being replaced by tris(tetra-n-butylammonium) hydrogenpyrophosphate (prepared according to Example 1) for the preparation of the intermediate compound: α,β di-[3-methyl-3-butene-1-yl] diphosphate.

EXAMPLE 10

Measurement of Antigenic Activity by Stimulation of the Proliferation of Tγ9δ2 lymphocytes in a Culture 20 microliters of the aqueous solution of the compound according to the invention adjusted to the final concentration specified in the test are added to an in vitro culture of $10^6$ total T lymphocytes in 1 ml, separated from the blood of a healthy adult human donor and initially containing 1-5% of Tγ9δ2 lymphocytes, in an adequate culture medium (RPMI 1640+ 10% of inactivated human serum and 50 U/ml of human interleukin-2 (hIL-2)). After culturing for 4 days, 50 U of dIL-2 are added per milliliter of culture medium. After 8 days, the cells are counted, collected, washed with phosphate buffer, and the Tγ9δ2 type cells are detected in the culture by labeling with conventional commercial reagents (fluorescein-labeled monoclonal antibodies) and the proportion thereof determined by flux cytometry analysis. The parameter measured is either the change in the proportion of or the increase in the number of Tγ9δ2 cells in cultures in the presence of the compound according to the invention in comparison with cultures not containing a compound according to the invention. The results of this testing are represented by plotting curves of these values (y-axis in FIG. 1) as a function of concentration on a logarithmic scale of the compound according to the invention placed in the culture (x-axis in FIG. 1).

FIG. 1 shows the results obtained with the compounds according to the invention obtained in Examples 1 (BrHPP)

and 2 (IHPP), with the dotted line being a negative control (value obtained in the absence of the compound according to the invention).

Figure 2:
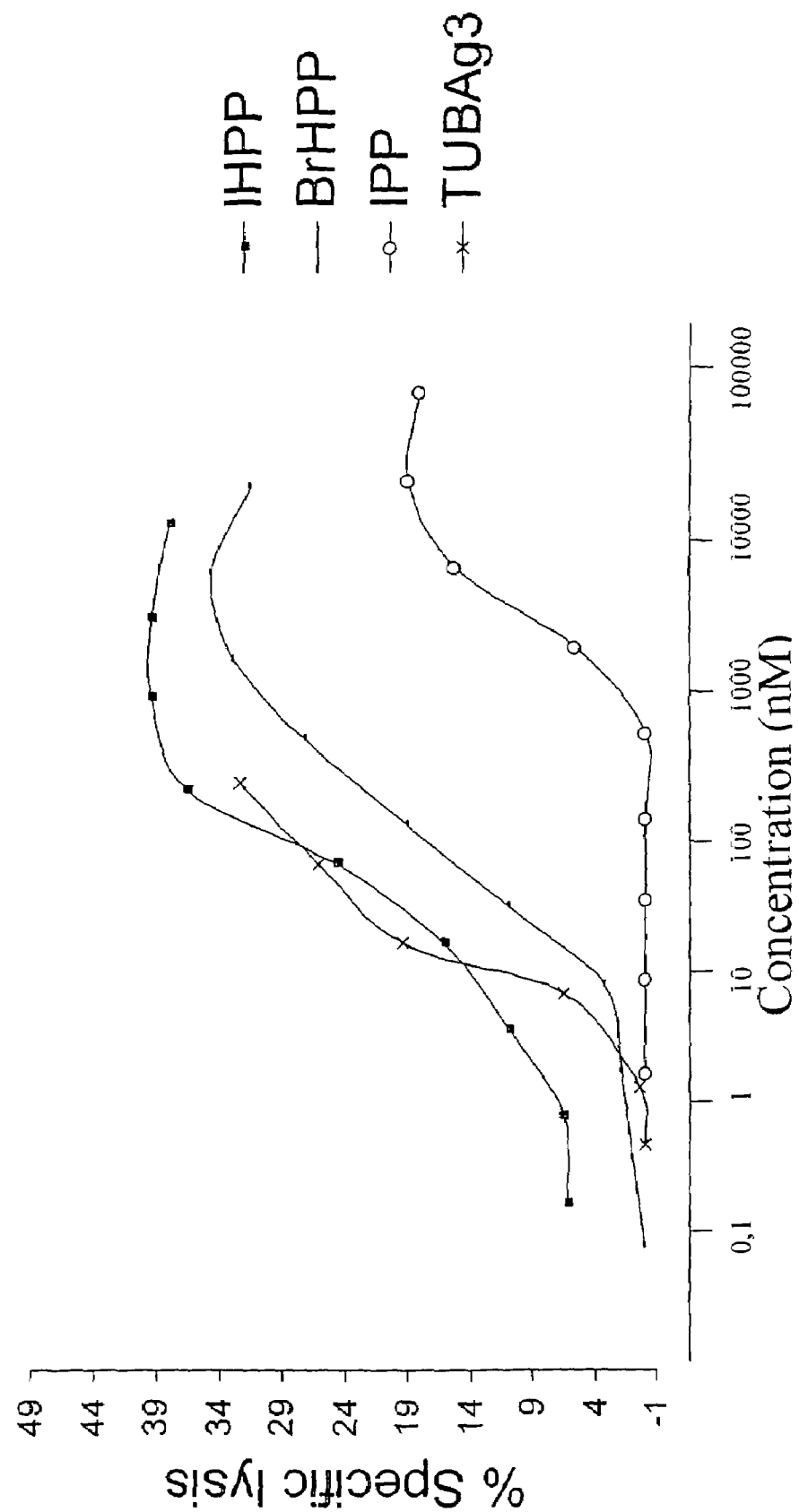
FIG. 2 is a graph showing the results obtained in Example 11.

Table 1 below shows the ED50 values, the effective dose at 50% of the maximum polyclonal lymphocyte amplification effect obtained as stated above with various compounds according to the invention.

squares in FIG. 2), of the compound IHPP according to the invention obtained in Example 2 (curve represented by white circles in FIG. 2) and of isopentenyl pyrophosphate IPP (curve represented by black triangles in FIG. 2).

It may be noted that the compounds according to the invention are active at a concentration of the order of 10 nM, which is of the same order as that of the natural phosphoantigen

TABLE I

| MOLECULE | | | ED 50% |
|---|---|---|---|
| Name | Abbreviation | Structure | nM |
| isopentenyl pyrophosphate | IPP | $CH_3-\underset{\parallel}{C}(=CH_2)-(CH_2)_2-OPP$ | 3000 |
| 3-(chloromethyl)-3-butanol-1-yl diphosphate | ClHPP | $CH_3-\underset{OH}{\overset{CH_2Cl}{C}}-(CH_2)_2-OPP$ | 100 |
| 3-(bromomethyl)-3-butanol-1-yl diphosphate | BrHPP | $CH_3-\underset{OH}{\overset{CH_2Br}{C}}-(CH_2)_2-OPP$ | 10 |
| 3-(iodomethyl)-3-butanol-1-yl diphosphate | IHPP | $CH_3-\underset{OH}{\overset{CH_2I}{C}}-(CH_2)_2-OPP$ | 3 |
| 3-(bromomethyl)-3-butanol-1-yl triphosphate | BrHPPP | $CH_3-\underset{OH}{\overset{CH_2Br}{C}}-(CH_2)_2-OPPP$ | 120 |
| 3-(iodomethyl)-3-butanol-1-yl triphosphate | IHPPP | $CH_3-\underset{OH}{\overset{CH_2I}{C}}-(CH_2)_2-OPPP$ | 70 |
| α, γ di-3-(bromomethyl)-3-butanol-1-yl triphosphate | di-BrHTP | $H_3C-\underset{OH}{\overset{CH_2Br}{C}}-(CH_2)_2-OPPPO-(CH_2)_2-\underset{OH}{\overset{CH_2Br}{C}}-CH_3$ | 3000 |
| α, γ di-3-(iodomethyl)-3-butanol-1-yl triphosphate | di-IHTP | $H_3C-\underset{OH}{\overset{CH_2I}{C}}-(CH_2)_2-OPPPO-(CH_2)_2-\underset{OH}{\overset{CH_2I}{C}}-CH_3$ | 7000 |

EXAMPLE 11

Measurement of Antigenic Activity by Stimulation of Induced Cytotoxicity

The specific cytotoxic activity of a Tγ9δ2 lymphocyte clone measured in accordance with the induced cytotoxicity test is compared, said activity being stimulated with decreasing concentrations of the phosphoantigen Tubag3 obtained as described by WO 95/20673 (curve represented by black diamonds in FIG. 2), of the compound BrHPP according to the invention obtained in Example 1 (curve represented by black Tubag3, whereas the prior art compound IPP is active at a concentration of the order of 3 μM, or 300 times higher.

EXAMPLE 12

Toxicity of BrHPP (Sodium Salt)

Eight 30 g mice received an intravenous injection (caudal vein) of 300 μl of PBS buffer containing 1 mg of BrHPP (sodium salt). No sign of shock or pyrogenicity is observed: 8 mice are still alive after 30 days; no significant variation in the weight of the mice is recorded during the study. Toxicity is thus less than 12.5% for a dose of 33.4 mg of BrHPP (Na⁺) per kilogram of animal body weight.

EXAMPLE 13

Pyrogenicity of BrHPP (Sodium Salt)

This test is performed in accordance with a protocol specified by standards ISO-10993-11 (1993) and USP XXIII. The test involves assessing the febrile reaction in rabbits after intravenous administration of BrHPP (sodium salt) at 400 μg/ml (i.e. 10 ml of extract per kilogram) to three rabbits. Temperature is taken every 30 minutes for 3 hours starting 30 minutes after the injection.

Only one rabbit exhibited an increase in temperature of greater than 0.5° C. (minimum threshold). On injection of the 400 μg/ml solution, the rabbits exhibited a side-effect talding the form of muscle tremors. Another rabbit injected with the same solution diluted 1:40, namely to 10 μg/ml, in 19 minutes exhibited no reaction to the injection.

EXAMPLE 14

In vivo Bioactivity of BrHPP (Sodium Salt) in the Macaque

These tests are performed on monkeys of the species *Macaca fascicularis* (males weight 3-4 kg) anaesthetized with 15 mg/kg Zoletil (zolazepam)®/0.01 mg/kg atropine. The batches of BrHPP (in NA⁺ form) are subjected to prior purity testing (>99%), quantified and have been tested in accordance with the pyrogenicity tests of Example 12. The animals are injected by rapid intravenous injection (2-5 minutes into the saphenous vein) with 0.1 mg/kg of BrHPP (i.e. 0.3-0.4 mg per animal) diluted in 10 ml of Ringer lactate. Each animal also receives a subcutaneous injection of 90,000 units of interleukin-2 (IL-2). These injections are performed once daily for four days. Control animals receive only the subcutaneous injection of IL-2 once daily for four days.

The proportion of Tγ9δ2 lymphocytes in total lymphocytes in the various animals is compared in the following three situations:
  in the animal's bloodstream,
  in a culture of total lymphocytes taken from the animal receiving only BrHPP,
  in a culture of total lymphocytes talken from the animal receiving BrHPP+IL-2.

The results are shown in Table II below:

TABLE II

| Animals injected: | % of Tγ9δ2 lymphocytes in the blood in vivo (7 days after injection) | Reactivity ex vivo of Tγ9δ2 lymphocytes (% after 10 days' culturing in vitro) | |
|---|---|---|---|
| | | Amplification by 40 nM BrHPP | Amplification by 40 nM BrHPP + IL-2 |
| Controls or IL-2 only | ~1%* [0.8-1.4] | 1% | ~8% [4.7-12] |
| BrHPP only | ~1% | 1% | ~11% [10-12] |
| BrHPP only, twice (1 injection + 1 booster) | ~1% | 1% | 40.2% |
| BrHPP + IL-2 | 7% [5-10] | 10% | 50.0% |

It may be noted that the single or repeated intravenous injection of BrHPP alone preactivates the monkey's Tγ9δ2 lymphocytes, but does not stimulate the growth thereof in the animal. The injection of BrFPP alone brings about preactivation of the Tγ9δ2 lymphocytes, which is in particular manifested by expression of the growth factor IL-2 from the surface of the receptor cells. In contrast, intravenous injection of BrHPP in the presence of subcutaneous IL-2 preactivates these same cells and brings about the growth thereof in vivo. Injection of the growth factor IL-2 alone brings about no specific response in the Tγ9δ2 lymphocytes.

We claim:
1. A compound selected from the group consisting of:

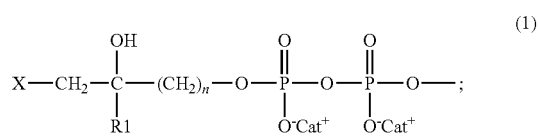

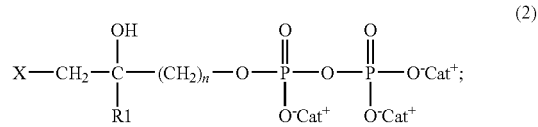

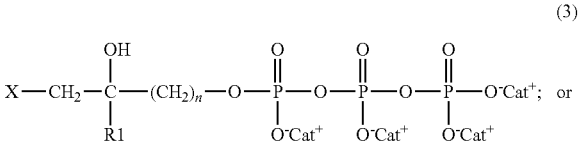

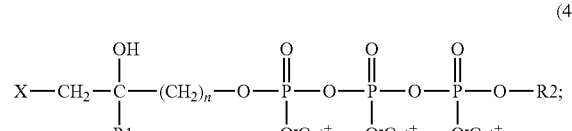

wherein:
X is a halogen;
n is 2 to 20;
Cat⁺ is a cation;
R1 is methyl or ethyl; and

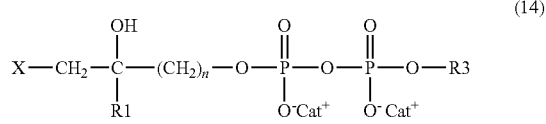

where X is a halogen selected from the group consisting of iodo, bromo, and chloro substituent,
R1 is methyl or ethyl,
Cat⁺ is a cation,
n is an integer between 2 and 20
R3 is:
  a halohydrin group of the formula:

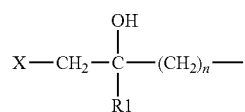

an epoxide group of the formula:

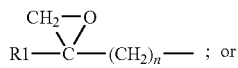

; or an alkene group of the formula:

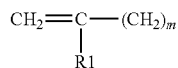

m being an integer between 1 and 20.

2. The compound according to claim 1, wherein n is 2 and R1 is methyl.

3. The compound according to claim 1, wherein said compound is

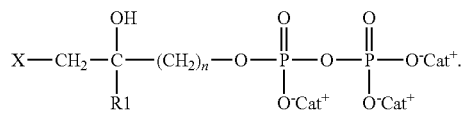
(2)

4. The compound according to claim 3, wherein n is 2 and R1 is methyl.

5. The compound according to claim 1, wherein said compound is

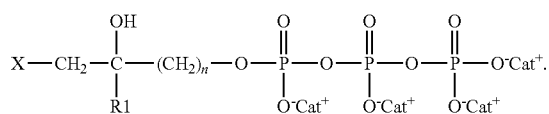
(3)

6. The compound of claim 5, wherein n is 2 and R1 is methyl.

7. A composition comprising an excipient and a compound according to claim 1.

8. The composition according to claim 7, wherein said compound is

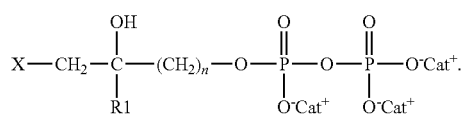
(2)

9. The composition according to claim 8, wherein n is 2 and R1 is methyl.

10. The composition according to claim 8, wherein n is 2, R1 is methyl and X is Br.

11. The composition according to claim 7, wherein said compound is

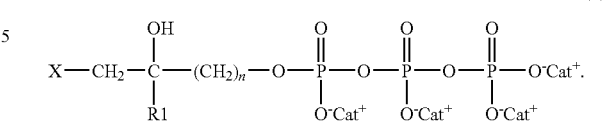
(3)

12. The composition according to claim 11, wherein n is 2 and R1 is methyl.

13. A composition comprising from 0.1 μg to 100 μg of a compound according to claim 1 and an excipient.

14. The composition according to claim 13, wherein said compound is

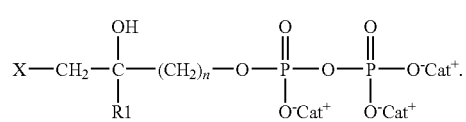
(2)

15. The composition according to claim 14, wherein n is 2 and R1 is methyl.

16. The composition according to claim 14, wherein n is 2, R1 is methyl and X is Br.

17. The composition according to claim 13, wherein said compound is

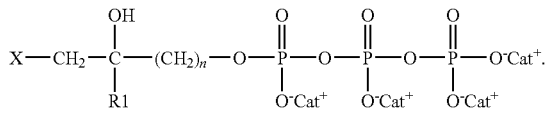
(3)

18. The composition according to claim 17, wherein n is 2 and R1 is methyl.

19. A method of inducing an immune response to a vaccine antigen comprising the administration of a composition comprising a vaccine composition and a compound according to claim 1.

20. The method according to claim 19, wherein said compound is

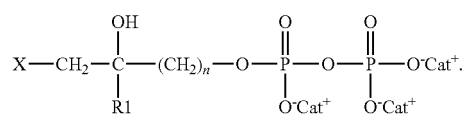
(2)

21. The method according to claim 20, wherein is 2, R1 is methyl and X is Br.

22. The method according to claim 20, wherein n is 2 and R1 is methyl. R1 is methyl and X is Br.

23. The method according to claim 19, wherein said compound is

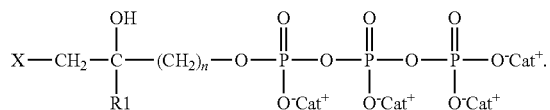
(3)

24. The method according to claim 23, wherein n is 2 and R1 is methyl.

25. A method of activating Tγ9δ2 lymphocytes in vivo, comprising administering to a patient in need thereof a composition comprising an effective amount of IL-2 in combination with an effective amount of a phosphohalohydrin compound according to claim 1.

26. The method according to claim 25, wherein said compound is

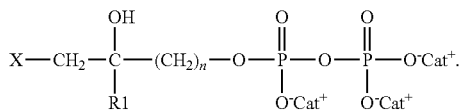
(2)

27. The method according to claim 26, wherein n is 2 and R1 is methyl.

28. The method according to claim 26, wherein n is 2, R1 is methyl and X is Br.

29. The method according to claim 25, wherein said compound is

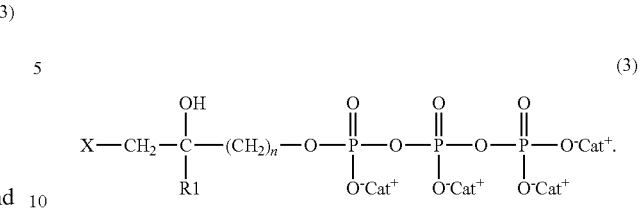
(3)

30. The method according to claim 29, wherein n is 2 and R1 is methyl.

31. The method according to claim 25, wherein said compound is

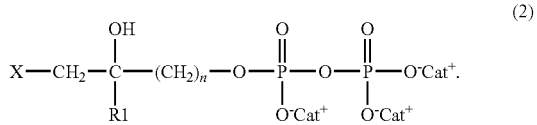
(2)

32. The method according to claim 31, wherein n is 2 and R1 is methyl.

33. The method according to claim 31, wherein n is 2, R1 is methyl and X is Br.

\* \* \* \* \*

UNITED STATES PATENT AND TRADEMARK OFFICE
CERTIFICATE OF CORRECTION

PATENT NO. : 7,625,879 B2  Page 1 of 2
APPLICATION NO. : 11/512688
DATED : December 1, 2009
INVENTOR(S) : Christian Belmant et al.

It is certified that error appears in the above-identified patent and that said Letters Patent is hereby corrected as shown below:

Column 7,
Line 15, "tetralcis(tetra-n-butylammonium)" should read
--tetrakis(tetra-n-butylammonium)--.

Column 12,
Lines 1-4, " $(14b) \xrightarrow{\text{OH}}_{\text{Basic medium } 0 \leq 25° \text{ C.}}$ " should read -- $(14b) \xrightarrow{\text{OH}^-}_{\text{Basic medium } 0 \leq 25° \text{ C.}}$ --.

Column 17,
Lines 12-13, "tetra-n-butylanrrnonium" should read --tetra-n-butylammonium--.
Line 14, "acetontrile" should read --acetonitrile--.
Line 53, "shaling" should read --shaking--.
Line 58, "amrnonium" should read --ammonium--.

Column 19,
Line 12, "3-(chloromethyl)-3-butano-1-1-yl" should read
--3-(chloromethyl)-3-butanol-1-yl--.
Line 57, "tetrakis(tetra-n-butylamnrnonium)" should read
--tetrakis(tetra-n-butylammonium)--.

Column 20,
Line 1, "tetralcis(tetra-n-butylammonium)" should read
--tetrakis(tetra-n-butylammonium)--.
Line 37, "300 mmol"should read --300 nmol--.
Line 40, "429 μof" should read --429 μl of--.

Column 21,
Line 6, "Ionpac®" should read --IonPac®--.
Lines 53-54, "y-[3-methyl-3-butene-l-yl]" should read --γ-[3-methyl-3-butene-l-yl]--.
Line 63, "IonPac®) AS11" should read --IonPac® AS11--.

Signed and Sealed this

Thirty-first Day of August, 2010

David J. Kappos
*Director of the United States Patent and Trademark Office*

CERTIFICATE OF CORRECTION (continued)
U.S. Pat. No. 7,625,879 B2

Column 25,
Line 17, "talding" should read --taking--.
Line 47, "talken" should read --taken--.

Column 26,
Line 4, "BrFPP" should read --BrHPP--.

Lines 17-38, " 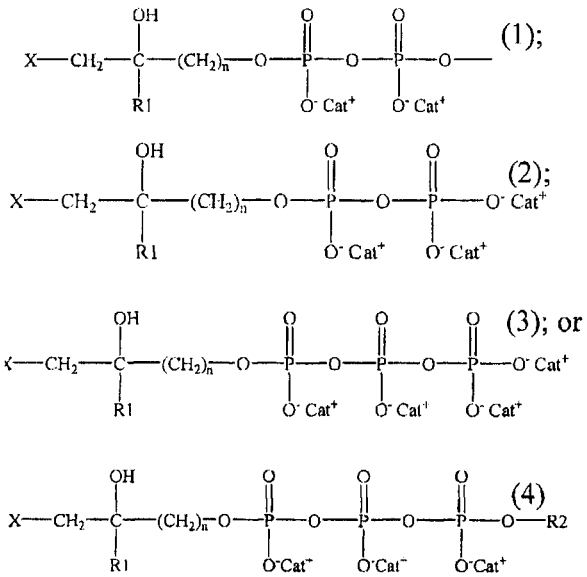 " should read

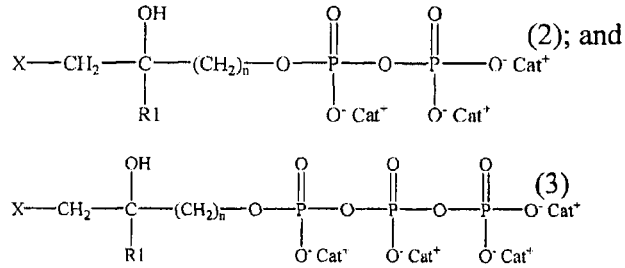

--.

Column 28,
Lines 61-62, "wherein is 2, R1 is methyl and X is BR." should read
 --wherein is 2, R1 is methyl.--.
Lines 64-65, "wherein n is 2 and R1 is methyl. R1 is methyl and X is BR." should read
 --wherein n is 2 and R1 is methyl and X is BR.--.